US010260022B2

(12) United States Patent
Berthier et al.

(10) Patent No.: US 10,260,022 B2
(45) Date of Patent: Apr. 16, 2019

(54) MICROCAPSULES IMPARTING INTENSE VANILLA ODOR NOTE

(71) Applicant: Firmenich SA, Geneva (CH)

(72) Inventors: Damien Berthier, Geneva (CH); Geraldine Leon, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/547,564

(22) PCT Filed: Feb. 5, 2016

(86) PCT No.: PCT/EP2016/052522
§ 371 (c)(1),
(2) Date: Jul. 31, 2017

(87) PCT Pub. No.: WO2016/124746
PCT Pub. Date: Aug. 11, 2016

(65) Prior Publication Data
US 2018/0023033 A1 Jan. 25, 2018

(30) Foreign Application Priority Data
Feb. 6, 2015 (EP) .................................... 15154226

(51) Int. Cl.
*A61K 8/11* (2006.01)
*C11B 9/00* (2006.01)
*A61Q 13/00* (2006.01)
(Continued)

(52) U.S. Cl.
CPC .............. *C11B 9/0061* (2013.01); *A61K 8/11* (2013.01); *A61K 8/84* (2013.01); *A61Q 13/00* (2013.01); *B01J 13/06* (2013.01); *B01J 13/08* (2013.01); *B01J 13/10* (2013.01); *B01J 13/14* (2013.01); *B01J 13/16* (2013.01); *C11D 3/001* (2013.01); *C11D 3/505* (2013.01); *A61K 2800/412* (2013.01); *A61K 2800/56* (2013.01)

(58) Field of Classification Search
CPC ............ A61K 8/11; A61K 8/84; C11B 9/0061
See application file for complete search history.

(56) References Cited

U.S. PATENT DOCUMENTS 2,800,457 A   7/1957   Green et al.
2,800,458 A   7/1957   Green et al.
(Continued)

FOREIGN PATENT DOCUMENTS

EP   1741775 B1   4/2009
GB   2432843 A    6/2007
(Continued)

OTHER PUBLICATIONS

International Search Report and Written Opinion, application PCT/EP2016/052522 dated Apr. 18, 2016.
(Continued)

*Primary Examiner* — John R Hardee
(74) *Attorney, Agent, or Firm* — Winston & Strawn LLP (57) ABSTRACT

The present invention relates to microcapsules delivering long lasting and intense vanilla-based odor note. More particularly, the present invention concerns a microcapsule comprising between 10% and 30% by weight, relative to the total weight of the microcapsule, of a particular perfuming ingredient imparting a vanilla-based odor note, which can be used in perfuming compositions and perfuming consumer products.

13 Claims, 3 Drawing Sheets

(51) Int. Cl.
*A61K 8/84* (2006.01)
*B01J 13/16* (2006.01)
*C11D 3/50* (2006.01)
*B01J 13/08* (2006.01)
*B01J 13/10* (2006.01)
*B01J 13/14* (2006.01)
*B01J 13/06* (2006.01)
*C11D 3/00* (2006.01)

(56) References Cited

U.S. PATENT DOCUMENTS

| | | | |
|---|---|---|---|
| 4,396,670 A | 8/1983 | Sinclair et al. | |
| 2007/0202063 A1 | 8/2007 | Dihora et al. | |

FOREIGN PATENT DOCUMENTS

| | | |
|---|---|---|
| GB | 2432850 A | 6/2007 |
| GB | 2432851 A | 6/2007 |
| GB | 2432852 A | 6/2007 |
| WO | WO2001041915 A1 | 6/2001 |
| WO | WO2004022221 A1 | 3/2004 |
| WO | WO2005054422 A1 | 6/2005 |
| WO | WO2007004166 A1 | 1/2007 |
| WO | WO2007062733 A1 | 6/2007 |
| WO | WO2007062833 A1 | 6/2007 |
| WO | WO2008016684 A1 | 2/2008 |
| WO | WO2011132098 A1 | 10/2011 |
| WO | WO2011161618 A1 | 12/2011 |
| WO | WO2012107323 A1 | 8/2012 |
| WO | WO2014059087 A2 | 4/2014 |

OTHER PUBLICATIONS

Bone et al. Chimia, 2011, vol. 65, n° 3, p. 177-181.
Dietrich et al., Acta Polymerica, 40 (1989), n° 4, p. 243-251.
Dietrich et al., Acta Polymerica, 40 (1989), n° 5, p. 325-331.
Dietrich et al., Acta Polymerica, 40 (1989), n° 11, p. 683-690.
Dietrich et al., Acta Polymerica, 1990, vol. 41, n° 2, p. 91.
Lee et al., J. Microencapsulation, 2002, vol. 19, p. 559-569.

MICROCAPSULES IMPARTING INTENSE VANILLA ODOR NOTE

RELATED APPLICATIONS

This application is a national stage application under 35 U.S.C. § 371 filing of International Patent Application PCT/EP2016/052522, filed Feb. 5, 2016, which claims the benefit of European patent application no. 15154226.3 filed Feb. 6, 2015.

TECHNICAL FIELD

The present invention relates to the field of perfume delivery systems. More particularly, the present invention relates to microcapsules capable of imparting a vanilla odor note with superior intensity and long lasting effect. The invention concerns capsules containing in their core high levels of a compound of formula (I)

wherein R groups represent, independently from each other, an hydrogen atom or a methyl group; as well as perfuming compositions and perfumed articles containing these capsules.

BACKGROUND

One of the problems faced by the perfume industry lies in the relatively rapid loss of the olfactive benefit provided by odoriferous compounds as a result of their volatility, particularly that of "top-notes". Also, some fragrance ingredients can be unstable in applications of functional perfumery and get lost due to degradation or to rapid evaporation.

In particular, most commonly used ingredients for imparting vanilla-type odor notes such as vanillin (4-hydroxy-3-methoxybenzaldehyde) and ethyl vanillin (3-ethoxy-4-hydroxybenzaldehyde) are known to rapidly decompose in challenging medium such as consumer product bases and to lead to the coloration of the products. Thus, there is a need for providing them in an encapsulated form not only to protect them but also in order to deliver long lasting vanilla notes in challenging medium such as consumer product bases. However, those ingredients cannot be encapsulated in a classical way at a sufficient loading to provide satisfactory effect from an odor perspective at a reasonable cost. Furthermore, when encapsulated, vanillin and ethyl vanillin are known to have a particular tendency to diffuse through the shell of microcapsules especially when added to consumer products which contains surface active ingredients.

In WO2014059087, these issues have been tackled. As a proposed solution for providing vanillin in an encapsulated form, core-shell microcapsules are described as being formed by combining vanillin and/or ethyl vanillin with a preformed core-shell microcapsule slurry or formulation and then aging the mixture for a time sufficient for vanillin and/or ethyl vanillin and microcapsules to interact. However, this process presents the drawback of requiring an extra step compared to standard encapsulation and implies that the shell of microcapsules comprising vanillin and/or ethyl vanillin as described in this application is permeable. So this process does not allow obtaining microcapsules with a controllable final amount of vanillin and/or ethyl vanillin inside the core of the capsule and the diffusion upon storage in challenging medium is not prevented. Furthermore, this process does not allow encapsulating large amounts vanillin and/or ethyl vanillin as the majority of these ingredients actually stay in the slurry as shown in the experimental part below.

There is therefore still a need to provide microcapsules susceptible of imparting a vanilla odor note when needed, having a high and controllable loading of perfuming compound responsible of the vanilla-based note inside the core of the microcapsules, using straightforward encapsulation process and without being limiting to permeable shells only.

The present invention provides a solution to the above mentioned problem with microcapsules comprising high loadings of a compound of formula (I) as defined above as part of a perfume oil in the core and comprising a shell with a permeability that can be chosen as a function of use and desired effect of the microcapsules. The compounds of formula (I) have been reported in WO2011132098 as perfuming ingredients conferring an odor of sweet vanilla type very close to the odor of vanillin, but were not expected to be possibly encapsulated at particularly high loadings, to impart an intense note and to circumvent stability issue in aggressive medium of capsules based on vanillin and ethyl vanillin.

SUMMARY OF THE INVENTION

The invention relates to a novel microcapsule comprising high loadings of a compound of formula (I)

wherein R groups represent, independently from each other, an hydrogen atom or a methyl group. Unexpectedly it has been found that contrary to vanillin or ethyl vanillin and despite their chemical similarity, the compounds of formula (I) could successfully be encapsulated at high levels with less leakage and could deliver a vanilla note with superior intensity than what was possible heretofore with those ingredients commonly used for imparting a vanilla odor note. The use of a capsule with a perfume oil comprising high amounts of a compound of formula (I) as a perfuming ingredient susceptible of delivering a vanilla odor note therefore overcomes the problems from the prior art and leads to an efficient and easily accessible vanilla delivery system.

A first object of the present invention is therefore a microcapsule comprising
A) a core comprising a perfume oil including a compound of formula (I)

wherein R groups represent, independently from each other, an hydrogen atom or a methyl group; and B) a polymeric shell surrounding said core;

characterized in that the compound of formula (I) is present in an amount comprised between 10% and 30% by weight, relative to the total weight of the microcapsule.

A second object of the present invention consists of the use of microcapsules as defined above in a perfuming composition or a perfumed consumer product, for delivering an intense and long lasting vanilla note.

A third object of the present invention is a method to confer, enhance, improve or modify a vanilla odor note comprising applying microcapsules as defined above to a surface.

Another object of the present invention is a perfuming composition comprising a) perfuming microcapsules, as defined above;

b) at least one ingredient selected from the group consisting of a perfumery carrier and a perfumery co-ingredient; and c) optionally at least one perfumery adjuvant.

A last object of the present invention is a perfuming consumer product comprising the microcapsules as defined above.

DETAILED DESCRIPTION OF THE INVENTION

Unless otherwise specified, percentages are meant to designate % by weight of a composition.

The microcapsules of this invention advantageously provide an efficient vanilla delivery system by using a compound of formula (I) as defined above at unexpected high levels in the core of the capsules. More particularly, compounds of formula (I) can surprisingly be incorporated as part of a perfume oil of microcapsules at higher amount compared to vanillin and ethyl vanillin without prejudice to the capsule stability and without particular requirements for the microcapsules formation, therefore allowing delivering an intense vanilla-based note in applications with flexibility regarding the capsule properties.

Therefore, a first object of the present invention is a microcapsule comprising

A) a core comprising a perfume oil including a compound of formula (I)

wherein R groups represent, independently from each other, an hydrogen atom or a methyl group; and B) a polymeric shell surrounding said core;

characterized in that the compound of formula (I) is present in an amount comprised between 10% and 30% by weight, relative to the total weight of the microcapsule.

According to the present invention, the compound of formula (I) can advantageously and surprisingly be incorporated in the core of the microcapsules at higher loadings than what is possible with vanillin and ethyl vanillin despite the structural similarity between all these compounds.

For the sake of clarity, "stability" in the present invention is mentioned in relation with the leakage of perfume oil out of the microcapsule when stored in an aggressive medium such as a consumer product base containing surfactants.

For the sake of clarity, "microcapsule" or the similar, in the present invention includes both morphologies such as core-shell systems (e.g. coacervates) and systems with a matrix morphology (e.g. extrudates or porous solid phases containing droplets of a liquid). By the terms "core-shell", it is meant that the perfume oil is a continuous phase surrounded by a shell whereas "matrix morphology" means that the perfume oil is dispersed in a matrix and surrounded by a shell.

Preferably the microcapsule according to the invention is a core-shell system.

By "perfume oil" (or also "perfume") it is meant here a perfume that is liquid at about 20° C. According to any one of the above invention embodiments said perfume oil includes a compound of formula (I), a solvent and optionally a perfuming co-ingredient or a perfuming composition. A perfuming co-ingredient is a perfuming ingredient other than a compound of formula (I). A "perfuming ingredient" is a compound, which is of current use in the perfumery industry, i.e. a compound which is used as active ingredient in perfuming preparations or compositions in order to at least impart a hedonic effect. In other words, such a perfuming ingredient must be recognized by a person skilled in the art of perfumery as being able to impart or modify in a positive or pleasant way the odor of a composition, and not just as having an odor. For the sake of clarity, the definition of a perfuming ingredient is meant to include also compounds that do not necessarily have an odor but are capable of modulating the odor, e.g. masking unpleasant odors. For the sake of clarity, the definition of perfuming ingredient is meant to include also pro-perfumes, i.e compounds which upon decomposition liberate a perfuming ingredient. A "perfuming composition" is a mixture of compounds including at least two perfuming co-ingredients.

In general terms, these perfuming ingredients belong to chemical classes as varied as alcohols, lactones, aldehydes, ketones, esters, ethers, ester nitriles, terpenoids, nitrogenous or sulphurous heterocyclic compounds and essential oils, and said perfuming ingredients can be of natural or synthetic origin. Specific examples of such perfuming ingredients can be found in reference texts such as the book by S. Arctander, "Perfume and Flavor Chemicals", published by the author, Montclair (New Jersey, USA), 1969, or its more recent versions, or in other work of a similar nature, as well as in the abundant patent literature in the field of perfumery. They are well known to the person skilled in the art of perfuming consumer products, that is, of imparting a pleasant odor to a consumer product. A non-exhaustive list of perfuming co-ingredients which shall be preferably used in combination with a compound of formula (I) includes those selected from the group consisting of coumarine, 1,3-Benzodioxole-5-carbaldehyde (origin: Firmenich SA, Switzerland), 3-hydroxy-2-methyl-4(4H)-pyranone 2-ethyl-3-hydroxy-4(4H)-pyranone, 4-methoxybenzaldehyde, veratryc aldehyde and gamma nonalactone.

The solvent is a hydrophobic solvent usable to form a capsule and of current use in the perfume industry. The solvent is preferably not an alcohol. Examples of such solvents are diethyl phthalate, isopropyl myristate, Abalyn® (rosin resins, available from Eastman), benzyl benzoate, limonene or other terpenes, benzyl salicylate, amyl salicylate, cyclohexyl salicylate, phenethyl phenyl acetate or isoparaffins. The solvent is preferably diethyl phthalate, isopropyl myristate, Abalyn®, benzyl benzoate, limonene or other terpenes, or isoparaffins. Even more preferably the solvent is benzyl benzoate.

The perfuming oil may also comprise adjuvants of current use in perfumery.

By "adjuvants of current use in perfumery" it is meant ingredients capable of imparting additional added benefits such as a color, chemical stability, etc. A detailed description of the nature and type of adjuvants commonly used in a perfuming oil is not required (and would not be exhaustive) as said ingredients are well known to a person skilled in the art.

The perfume oil can be present in various amounts depending on its nature and/or on the strength of the aimed olfactive effect. Typically, the microcapsule comprises, based on the total microcapsule weight, from about 1% to about 99% by weight of perfume oil. Preferably the microcapsule comprises from about 20% to about 96% by weight of perfume oil.

According to a particular embodiment, the perfume oil comprises compound of formula (I) and a solvent.

According to a particular embodiment, the perfume oil consists essentially of the compound of formula (I) and a solvent.

According to any one of the above embodiments, the compound of formula (I) is present in an amount comprised between 10 and 30% by weight relative to the total weight of the microcapsule, preferably between 15 and 30% by weight relative to total weight of the microcapsule. More preferably, the compound of formula (I) is present in an amount comprised between 20% and 30% by weight, relative to the total weight of the microcapsule. Most preferably the compound of formula (I) is present in an amount comprised between 25% and 29% by weight, relative to the total weight of the microcapsule.

According to a particular embodiment of the invention, one R group of the compound of formula (I) represents a hydrogen atom and the other R group represents a hydrogen atom or a methyl group. Preferably, the compound of formula (I) is 2-methoxy-4-methylphenyl methyl carbonate. Advantageously 2-methoxy-4-methylphenyl methyl carbonate, contrary to vanillin or ethyl vanillin, does not color upon aging in aggressive medium such as alcoholic compositions, soaps, shampoos or all-purpose cleaners.

Optionally, the core of the capsule may comprise in addition to the perfume oil, active agents, capable of bringing a benefit or effect into its surrounding environment, such as, in particular, flavoring, cosmetic, skin caring, malodor counteracting, bactericide, fungicide, antioxidant, antifoaming, agrochemical ingredient, and/or an insect repellent or attractant.

The component B) of the microcapsules according to the invention is a polymeric shell that can be obtained by a variety of processes which leaves flexibility with regard to the properties of the obtained delivery system. For example the polymeric shell can be more or less permeable. The presence of the compound of formula (I) in the core of the microcapsule does not limit the nature of the shell and is not detrimental to the stability of the microcapsule.

According to any embodiment of the invention, the polymeric shell is preferably based on aminoplast, polyamide, polyester, polyurea or polyurethane resins or a mixture thereof or is based on gel hydrophilic colloid. Said resins and shells are well known to a person skilled in the art and are described in more details below.

According to any embodiment of the invention, such a shell is preferably obtained by a phase separation process induced by polymerization, by interfacial polymerization, by coacervation or altogether. Such processes have been described in the prior art.

According to one embodiment of the invention, the core-shell microcapsules are obtained by a phase separation process induced by polymerization. Such a process is based on amino resins produced by the polycondensation of an aldehyde (e.g. formaldehyde, 2,2-dimethoxyethanal, glyoxal, glyoxylic acid or glycolaldehyde and mixtures thereof) with an amine, namely urea, benzoguanamine, glycoluryl, melamine, methylol melamine, methylated methylol melamine, imino melamine, guanazole and the like, as well as mixtures thereof. Examples of suitable ureas are dimethylol urea, methylated dimethylol urea, urea-resorcinol, and mixtures thereof.

Some of the seminal literature related to the encapsulation of perfumes by polycondensation of amino resins, namely melamine based resins with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670 to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinence, which also address the suitable uses of such microcapsules, are represented for example by the article of H. Y. Lee et al. in Journal of Microencapsulation, 2002, vol. 19, pages 559-569, international patent publication WO 01/41915 or yet the article of S. Bone et al. in Chimia, 2011, vol. 65, pages 177-181.

The polycondensation of an aldehyde with an amine or an amino resin leads to shells or walls consisting of highly cross-linked resins known as thermoset resins (aminoplast resins). Suitable alkylolated polyamines for the microcapsules according to the invention encompass mixtures of mono- or polyalkylolated polyamines, which in turn may be partially alkylated with alcohols having from 1 to 6 methylene units, and also encompass mono- or polymethylolmelamine and/or mono- or polymethylolurea precondensates, such as those commercially available under the trademark Urac® (origin: Cytec Technology Corp.), Cymel® (origin: Cytec Technology Corp.), Urecoll® or Luracoll® (origin: BASF).

Other suitable amino resins from the mixtures of mono- or polyalkylolated polyamines can be obtained by polycondensation of an aldehyde such as 2,2-dimethoxyethanal, glyoxal, glyoxylic acid or glycolaldehyde and mixtures thereof, and an amine, as described in WO2011/161618. Non-limiting examples of polyalkylolated polyamines from the polycondensation with 2,2-dimethoxyethanal comprise poly[N-(2,2-dimethoxy-1-hydroxy)] polyamines, mono- and di-[N-(2,2-dimethoxy)-1-hydroxy)] urea, mono-, di-, tri-, and/or tetra-[N-(2,2-dimethoxy)-1-hydroxy)] melamine, tetra-[N-(2,2-dimethoxy)-1-hydroxy)] glycouryl or di-[N-(2,2-dimethoxy)-1-hydroxy)] benzoguanidine. Non-limiting examples of polyalkylolated polyamines from the polycondensation with glyoxal comprise poly[N-(2-hydroxyacetaldehyde)] polyamines, mono- and di-[N-(2-hydroxyacetaldehyde)] urea, mono-, di-, tri-, and/or tetra-[N-(2-hydroxyacetaldehyde)] melamine, tetra-[N-(2-hydroxyacetaldehyde)] glycouryl or di-[N-(2-hydroxyacetaldehyde)] benzoguanidine. Non-limiting examples of polyalkylolated polyamines from the polycondensation with glyoxylic acid comprise poly[N-(2-hydroxyacetic acid)] polyamines, mono- and di-[N-(2-hydroxyacetic acid)] urea, mono-, di-, tri-, and/or tetra-[N-(2-hydroxyacetic acid)] melamine, tetra-[N-(2-hydroxyacetic acid)] glycouryl or di-[N-(2-hydroxyacetic acid)] benzoguanidine. Non-limiting examples of polyalkylolated polyamines from the polycondensation with glycolaldehyde comprise poly[N-(ethane-1,2-diol)] polyamines, mono- and di-[N-(ethane-1,2-diol)] urea, mono-, di-, tri-, and/or tetra-[N-(ethane-1,2-diol)] melamine, tetra-[N-(ethane-1,2-diol)] glycouryl or di-[N-(ethane-1,2-diol)] benzoguanidine.

According to an embodiment of the invention, core-shell microcapsules are obtained by interfacial polymerization, in which the core is encapsulated into a crosslinked polyurea or polyurethane shell or wall formed by reaction of an amino resin, a polyamine or polyol with at least one polyisocyanate.

A polyurea microcapsule shell or wall is formed when a polyamine or an amino resin is used. Particularly efficient polyamines are water soluble guanidine salts and/or guanidine and/or amino resins such as those described above. By "water soluble guanidine salt" it is meant a salt soluble in water and resulting from the reaction of guanidine with an acid. One example of such salts is guanidine carbonate.

In the case where a polyol is used as the cross-linker, a polyurethane microcapsule shell or wall is formed. As polyol, glycerol is preferred.

The use of specific proportions of polyisocyanate versus polyamine or polyol is advantageous. Therefore, preferably, for each mole of isocyanate group, 1 to 10, preferably 2 to 5 moles of amine or alcohol groups are present. Accordingly, there is added an excess of the cross-linking agent.

When a polyisocyanate compound is reacted with an amino resin, e.g. obtained by a phase separation process as described above, a polyamine or a polyol, any polyisocyanate is suitable for the reaction, but a polyisocyanate comprising at least two isocyanate groups or at least three isocyanate groups is preferred. Low volatility polyisocyanate molecules are preferred because of their low toxicity. In particular, the polyisocyanate can advantageously be selected from the group consisting of a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate (known with the tradename of Desmodur® N100, origin: Bayer) are even more preferred.

In case of phase separation process induced by polymerization, or interfacial polymerization, a polymeric stabilizer can be used to prevent the microcapsules from agglomerating, thus acting as a protective colloid which is added to the monomer mixture, intended to form the shell, prior to polymerization. For the sake of clarity, in the present context by the expression "stabilizer", or similar, it is understood the meaning usual in the art, i.e. a compound that is capable of, or is added to, stabilize the system, e.g. to prevent aggregation or agglomeration of the microcapsules, for example in the consumer product application or during the process for the microcapsule preparation. The use of said stabilizer is standard knowledge to the person skilled in the art.

For the purpose of the present invention, said stabilizer can be an ionic or non-ionic surfactant or a colloidal stabilizer. The exact nature of such stabilizers is well known to a person skilled in the art. As non-limiting examples one may cite the following stabilizers: non-ionic polymers such as polyvinyl alcohol (Mowiol 18-88, Origin: Fluka), cellulose derivatives such hydroxyethyl cellulose or carboxymethyl cellulose such as Ambergum™ 1221 (origin: Aqualon Hercules), polyethylene oxide, co-polymers of polyethylene oxide and polyethylene or polypropylene oxide, co-polymers of alkyl acrylates and N-vinylpyrrolidone; ionic polymers such as acrylic copolymers of acrylamide and acrylic acid such as Alcapsol® 144 (origin: Ciba), e.g. acid/acrylamide copolymers produced from a monomer mixture of acrylic acid and acrylamide wherein the acrylic acid content is in the range of from 20 to 80%, acid anionic surfactants (such as sodium dodecyl sulfate), acrylic co-polymers bearing a sulfonate group (such as sodium poly(styrene sulfonate), and co-polymers of vinyl ethers and maleic anhydride.

Optionally, the microcapsules obtained by phase separation process induced by polymerization or by interfacial polymerization may be coated with a cationic copolymer. The cationic polymer allows partial or complete neutralization of the negative electrical charge borne by the microcapsules, or even the conversion of the negatively-charged microcapsules into positively-charged microcapsules. To this effect, according to the invention, preferred cationic polymers comprise cationic polyacrylates and acrylamides such as Salcare® SC60 (origin: BASF), cationic cellulose derivatives, such as those available under the trademark Ucare® (origin: Amerchol), and quaternized guar gums available under the trademark Jaguar® (origin: Rhodia). Other cationic compounds that can be used include the polyquaternium compounds, all which have a plurality of quaternary ammonium groups, or polymeric species such as diallyl dimethyl ammonium chloride/acrylamide polymers such as those available under the trade name Merquat® (origin: Nalco).

According to an embodiment of the invention, core-shell microcapsules are obtained by coacervation, in which the core is encapsulated into a hydrogel shell.

The hydrogel shell comprises a protein and, optionally, a non-protein polymer and forms a coacervate around the hydrophobic droplet. Preferably, the non-protein polymer is charged oppositely to the protein. These materials are also referred to as hydrocolloids, that is polymeric substances that can be dissolved in water, optionally at elevated temperatures, e.g. up to 90° C. These encompass polymers such as proteins, polysaccharides and polyacids that are generally known to be useful in coacervation methods.

A coacervation process may be "simple" or "complex". The former designation is employed when a single protein is used to form a capsule wall as phase separation is taking place. The latter term designates the use of a second oppositely charged non-protein polymer to bring about phase separation. Complex coacervation method is widely practiced in commercial processes and has been well described in the literature. In particular U.S. Pat. No. 2,800,457 and U.S. Pat. No. 2,800,458 disclose complex coacervation in a very detailed manner.

Proteins useful in coacervation processes include albumins, vegetable globulins and gelatines. The molecular weight of the protein is typically in the order of 40'000 to 500'000 preferably 20'000 to 250'000. Some protein aggregates, however, may have molecular weights even greater than this.

Typical non-protein polymers useful in complex coacervation methods include, in particular, negatively charged polymers. For example, they may be selected from gum arabic, xanthan, agar, alginate salts, cellulose derivatives, for example carboxymethyl cellulose, pectinate salts, carrageenan, polyacrylic and methacrylic acid, and/or mixtures thereof. Further suitable non-proteins can be derived from the literature, for example from WO 2004/022221, page 4, lines 27-29.

The protein and, optionally, non-protein polymers are usually dissolved in water to form a hydrocolloid solution. Preferably, in the aqueous hydrocolloid solution, the protein is present in an amount of from 0.5 to 3.5 wt %, more preferably from 1 to 2 wt %.

If present, the amount of non-protein polymer is preferably from 0.5 to 3.5 wt %, more preferably from 1 to 2 wt % in the aqueous solution.

In a particular embodiment, the weight ratio between the protein and the non-protein polymer is from about 3:1 to 1:3, more preferably 2:1 to 1:1, most preferably about 3:2.

Optionally, a cross-linking agent is typically used to harden the coating layer. Suitable cross-linking agents include formaldehyde, acetaldehyde, glutaraldehyde, glyoxal, chrome alum, or transglutaminase. Preferably, transglutaminase is used at 10-100, preferably 30-60 activity units per gram of gelatine. This enzyme is well described and commercially obtainable.

According to any embodiment of the invention, the average size of the microcapsules may range between 1 micrometer to 1000 micrometers, or even more, depending on the mixing shear stress applied to the system during microcapsule formation. The selection of the most appropriate range and distribution of size depends on the application for which the microcapsules are intended, and can be controlled and adjusted by the skilled person as a function of the latter. In a general manner the average size of the microcapsules according to the invention ranges between 1 micrometer and 600 micrometers and, more preferably, comprises a range of 1 to 200 micrometers.

The phase separation process induced by polymerization, the interfacial polymerization process and coacervation described above essentially convert emulsions, consisting of a dispersed perfume oil, comprising compound of formula (I) to be encapsulated and a continuous water phase, into a dispersion of solid beads consisting of a core surrounded by a shell, whose permeability depends on a number of factors, including the extent of cross-linking, and/or the thickness of the shell. A person skilled in the art is able to easily find optimal factors and conditions to obtain capsules with shell having the desired permeability.

According to any embodiment of the invention, the invention's microcapsules obtained either by phase separation, polycondensation or by interfacial polymerization have a shell thickness varying between 10 to 1000 nm, preferably between 20 and 500 nm, even more preferably between 25 and 350 nm. As an example, the capsule's shell thickness can be determined by atomic force microscopy (AFM) or scanning electron microscopy (SEM). The amount and nature of monomer used to form the shell allow varying the shell thickness and so its permeability. For example, when the resin type is the same, the use of less monomer for preparing the microcapsule resin generally provides thinner wall capsules. A higher amount of the monomer creates a less permeating barrier, while a lower amount provides a barrier that is permeated more easily. Yet another way would be to vary the monomer type of the microcapsules. For example, aromatic isocyanates such as Takenate® monomers provide a less permeating barrier while aliphatic isocyanates such as Desmodur® N100 monomers provide a more permeating barrier. In addition, the perfume oil can be encapsulated in different ways to achieve this difference, such as by solid wall-encapsulation (for a greater barrier effect) compared to matrix encapsulation (for a lesser barrier effect). The skilled person in the art can select these different features by routine testing depending upon the specific perfume oil ingredients to be included in the mixtures with 2-methoxy-4-methylphenyl methyl carbonate.

According to any embodiment of the invention, the microcapsules of the present invention may be characterized by a nominal shell to core mass ratio lower than 40%, preferably lower than 20% and, most preferably, lower than 10%. Hence, the microcapsules may have extremely thin and frangible shells. The shell to core ratio is obtained by measuring the effective amount of encapsulated perfume microcapsules that have been previously washed with water and separated by filtration. This is achieved by extracting the wet microcapsule cake by microwave-enhanced solvent extraction and subsequent gas chromatographic analysis of the extract. Nominal shell to core mass ratio has a strong influence on the performance of the delivery system in term of stability in challenging medium but also in term of olfactive performance. A skilled person in the art is capable to set up the most appropriate nominal shell to core mass ratio to obtain microcapsule with an appropriate performance in relation to the use of the microcapsule.

The microcapsules of the present invention are provided in the form of aqueous slurries, having typically 20 to 55% of solid content, where the term "solid content" is relative to the total weight of the microcapsules. The slurry comprises microcapsules, water and precursor materials for making the microcapsules. The slurry may comprise other minor ingredients, such as an activator for the polymerization process and/or a pH buffer. To the slurry, a formaldehyde scavenger may be added.

According to a particular embodiment, the capsule slurry obtained by any of the above-mentioned processes can further be dried. Any drying method known to a skilled person in the art can be used including, but not limited to fluidized bed or spray-drying tower with co-current or counter current air streams with atomizing devices of different configuration, such as two-fluid nozzles, rotary nozzles or ultrasonic nozzles. In particular the slurry may be spray-dried preferably in the presence of a polymeric carrier material such as polyvinyl acetate, polyvinyl alcohol, dextrines, maltodextrines, glucose syrups, natural or modified starch, vegetable gums, gum acacia, pectins, xanthanes, alginates, carragenans or cellulose derivatives to provide microcapsules in a powder form. A broad range of suitable spray drying configurations is available from companies like GEA-Niro (Denmark).

According to a particular embodiment, the capsule slurry obtained by any of the above-mentioned processes can further be mixed with a thermoplastic carrier to be extruded by any extrusion method known to a skilled person such as, but not limited to, spheronization, gear-pump, piston extrusion, single screw extrusion, twin-screw co-rotating extrusion, twin-screw counter rotating extrusion. Twin-screw extruders can have different screw configurations to get mixing zones, melting zones, homogenizing zones or venting zones and the like as is conventionally known in the art. The resulting molten mass embedding the capsules of the present invention can be further processed to be granulated by any methods including but not limited to quenching, grinding, die-face pelletization, molding. A broad range of suitable extrusion configurations is available from companies like Brabender or Coperion (Germany). By the term "thermoplastic carrier", it is meant the normal meaning understood by a person skilled in the art, i.e. that a thermoplastic carrier is a material which becomes soft above a certain temperature and becomes hard when cool. When the material is in a soft state, it could be shaped. This material could be heated several times without losing its thermoplastic property.

The slurry may contain formulation aids, such as stabilizing and viscosity control hydrocolloids, biocides, and, as the case may be, formaldehyde scavengers.

The aqueous phase can also advantageously comprise hydrophilic inorganic particles such as silica particles or titanium oxide, in order to adjust the density of the microcapsules. By doing so, the density of the microcapsules can be brought to a value similar to that of the end product into which it is intended to incorporate them and therefore the microcapsules are maintained homogeneously suspended and dispersed in such liquid products. This is particularly advantageous in perfuming microcapsules because the specific gravity of the perfuming ingredients is usually lower than 1 g/ml.

The microcapsules according to the invention protect the perfume oil against premature degradation during storage in the application formulation and increase the deposition of the perfume oil on the target substrate once the latter is treated with the consumer product.

According any embodiment of the invention, one may use the microcapsules of the present invention as a mixture with a free oil phase and/or with other microcapsules or other types of delivering technologies of the prior-art.

Optionally, the microcapsules of the invention are washed via centrifugation and re-suspension several times. In another optional step, the microcapsules can be isolated from the slurry that is obtained from the processes described.

As shown in the examples below, the microcapsules of the invention provide particularly good delivery system imparting a vanilla odor note of superior intensity compared to encapsulated vanillin or ethyl vanillin.

In another aspect, the invention concerns the use of microcapsules described above in a perfuming composition or a perfumed consumer product for delivering a long-lasting and intense vanilla note. In other words, it concerns a method to confer, enhance, improve or modify a vanilla odor note comprising applying microcapsules as defined above to a surface.

The microcapsules of the invention can be advantageously used for the controlled release of the encapsulated vanilla perfume. It is therefore particularly appreciated to include these microcapsules as perfuming ingredients in a perfuming composition or in a perfumed consumer product. The invention also relates to methods of perfuming and malodor countering via the use of the microcapsules of the invention.

Therefore, another object of the present invention is a perfuming composition comprising:
  i) as perfuming ingredient, microcapsules as defined above;
  ii) at least one ingredient selected from the group consisting of a perfumery carrier and a perfuming co-ingredient; and
  iii) optionally at least one perfumery adjuvant.

By "perfumery carrier" we mean here a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents and in addition of solvent usable to form a capsule previously cited, such as dipropyleneglycol, 2-(2-ethoxyethoxy)-1-ethanol. For the compositions which comprise both a perfumery carrier and a perfuming co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

The term "perfuming co-ingredient" is equivalent to perfuming ingredient defined above. "Perfumery adjuvant" is as defined above.

An invention's composition consisting of the invention's microcapsules as defined above and at least one perfumery carrier represents a particular embodiment of the invention.

Furthermore, microcapsules as defined above or a perfuming composition comprising such microcapsules can also be advantageously used in all the fields of modern perfumery, i.e. fine or functional perfumery, to prevent the malodor formation and/or to positively impart or modify the odor of a consumer product and into which said microcapsules as defined above are added.

As shown in the examples below, the microcapsules of the invention provide a good olfactive performance and impart a vanilla-based odor note or superior intensity when the capsules are broken. They provide a controlled or triggered release of the encapsulated compound of formula (I), said compound being slowly released from the microcapsules, thus considerably improving the perfume long-lastingness and intensity.

Consequently, another object of the present invention is represented by a perfuming consumer product comprising, as perfuming ingredient, microcapsules as defined above.

The invention's microcapsules can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface) or in the ambient air. In other words, a perfuming consumer product according to the invention is a product which comprises the functional formulation, as well as optionally additional benefit agents, corresponding to the desired consumer product, e.g. a detergent or an air freshener, and an olfactive effective amount of at least one invention's microcapsules. For the sake of clarity, said perfuming consumer product is a non-edible product.

The nature and type of the constituents of the perfumery consumer product do not warrant a more detailed description here, which in any case would not be exhaustive, the skilled person being able to select them on the basis of his general knowledge and according to the nature and the desired effect of said product.

Non-limiting examples of suitable perfumery consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent or refresher; or a mal-odor neutralizing sanitary product; or a pet product in the form of absorbent pads, litters, cleansers and refreshing and perfuming sprays and products. Preferably, the consumer product is a fabric care product. Preferably, the consumer product is a soap bar or a liquid detergent.

The capsules of the invention may be used as such to perfume the consumer products, in which case the reaction mixture is directly added to a consumer product as defined in any of the above embodiments. Alternatively, the microcapsules of the invention may be isolated from the reaction mixture before being incorporated into the consumer product. Similarly, the reaction mixture comprising the microcapsules of the invention may be mixed with or sprayed onto a dry, powdered product, such as a washing powder or powdered detergent or the microcapsules may be dried and added to these products in solid form. The microcapsules may for example be spray-dried as defined above.

The proportions in which the microcapsules according to the invention can be incorporated into the various aforementioned articles or compositions vary within a wide range of values. These values are dependent on the nature of the article to be perfumed and on the desired organoleptic effect as well as the nature of the co-ingredients in a given base when the microcapsules according to the invention are mixed with perfuming co-ingredients, solvents or additives commonly used in the art.

For example, in the case of perfuming compositions, typical concentrations are in the order of 0.001% to 5% by weight, or even more, of the microcapsuless of the invention based on the weight of the composition into which they are incorporated. Concentrations lower than these, such as in the order of 0.01% to 1% by weight, can be used when these microcapsules are incorporated into perfumed articles, percentage being relative to the weight of the article.

Formulations of consumer product bases in which the microcapsules of the invention can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

The last object of the present invention is the use as a perfuming ingredient of a microcapsule as defined above for delivering a long lasting vanilla-based note.

EXAMPLES

The following non limiting examples are further illustrative of the present invention embodiments, and further demonstrate the advantages of the invention relative to prior art teachings.

Abbreviations have the usual meaning in the art and the temperatures are indicated in degrees centigrade (° C.).

Example 1

Preparation of Polyurea Microcapsules Comprising 2-Methoxy-4-Methylphenyl Methyl Carbonate and Control Polyurea Microcapsules Comprising Vanillin:

General Procedure for Polyurea Microcapsule Comprising 2-Methoxy-4-Methylphenyl Methyl Carbonate In a 200 mL reactor (Schmizo, Switzerland), a 30% solution of 2-methoxy-4-methylphenyl methyl carbonate in benzyl benzoate and Takenate® D-110N (Trimethylol propane-adduct of xylylene diisocyanate, origin: Mitsui Chemicals, Inc., Japan) was emulsified into a solution of poly(vinyl alcohol) (2 wt %, Mowiol® 18-88, Aldrich, Switzerland) with an ultra-turrax rotor stator at 24'000 rpm for 3 minutes (pH=5.1). A solution of guanidine carbonate in water was added dropwise at room temperature for 1 h under gentle stirring (300 rpm, anchor). The emulsion was warmed up from RT to 70° C. in 1 h and the reaction mixture was heated at 70° C. for an additional 2 h to afford a white capsule dispersion (pH 7.6).

Capsules A to C

Polyurea microcapsules according to the invention (Capsules A to C) were prepared following the general procedure described above with the following ingredients:

TABLE 1

Composition of Capsules A to C

| Ingredient | Capsules A Amount (g) | Capsules B Amount (g) | Capsules C Amount (g) |
|---|---|---|---|
| PVOH | 34.85 | 34.85 | 20.91 |
| Takenate ® D-110N[1] | 4.68 | 4.68 | 2.81 |
| Guanidine carbonate | 0.55 | 0.55 | 0.33 |
| Solution of benzyl benzoate containing 2-methoxy-4-methylphenyl methyl carbonate | 21 | 51 | 45.9 |
| Water | 10.85 | 10.85 | 6.51 |
| Oil concentration relative to the total weight of the microcapsule (wt %) | 81.5% | 91.5% | 94.1% |
| 2-methoxy-4-methylphenyl methyl carbonate concentration relative to the total weight of the microcapsule (wt %) | 24.5% | 27.4% | 28.2% |

[1]Trimethylol propane-adduct of xylylene diisocyanate, origin: Mitsui Chemicals, Inc., Japan Preparation of Control Polyurea Microcapsules Comprising Vanillin:
General Procedure for Polyurea Microcapsule Comprising Vanillin In a 200 mL reactor (Schmizo, Switzerland), a 10% solution of vanillin in benzyl benzoate and Takenate® D-110N (Trimethylol propane-adduct of xylylene diisocyanate, origin: Mitsui Chemicals, Inc., Japan) was emulsified into a solution of poly(vinyl alcohol) (2 wt %, Mowiol® 18-88, Aldrich, Switzerland) with an ultra-turrax rotor stator at 24'000 rpm for 3 minutes (pH=5.1). A solution of guanidine carbonate in water was added dropwise at room temperature for 1 h under gentle stirring (300 rpm, anchor). The emulsion was warmed up from RT to 70° C. in 1 h and the reaction mixture was heat at 70° C. for additional 2 h to afford a white capsule dispersion (pH 7.6).

Control Capsules D to F

Polyurea microcapsules comprising vanillin (Capsules D to F) were prepared following the general procedure described above with the following ingredients:

TABLE 2

Composition of Capsules D to F

| Ingredient | Capsules D Amount (g) | Capsules E Amount (g) | Capsules F Amount (g) |
|---|---|---|---|
| PVOH | 34.85 | 34.85 | 20.91 |
| Takenate ® D-110N[1] | 4.68 | 4.68 | 2.81 |
| Guanidine carbonate | 0.55 | 0.55 | 0.33 |
| Solution of benzyl benzoate containing vanillin | 21 | 51 | 45.9 |
| Water | 10.85 | 10.85 | 6.51 |
| Oil concentration relative to the total weight of the microcapsule (wt %) | 81.5% | 91.5% | 94.1% |
| Vanillin concentration relative to the total weight of the microcapsule (wt %) | 8.2% | 9.1% | 9.4% |

[1]Trimethylol propane-adduct of xylylene diisocynate, origin: Mitsui Chemicals, Inc., Japan The solution of vanillin in benzyl benzoate contained 10% of vanillin (maximum). It means that vanillin was present in an amount of 8.2%, by weight, relative to the total weight of the obtained microcapsules in capsules D, 9.1% in capsules E and 9.4% in capsule F.

Whereas the solution of 2-methoxy-4-methylphenyl methyl carbonate in benzyl benzoate could contain more than 10% of 2-methoxy-4-methylphenyl methyl carbonate, even more than 20%, and even more than 25%.

Three times more 2-methoxy-4-methylphenyl methyl carbonate compared to vanillin could be loaded in the core of the capsule.

Example 2

Olfactive Performance of Microcapsules of the Present Invention Compared to Control Microcapsules
Procedure for Microcapsules Deposition on Cotton A square of cotton fabric (12 cm×12 cm) was cut. A deposit zone was delimited in form of 10 centimeters diameter circle. For each capsule, four samples were analyzed in order to obtain a statistic measurement. Each dispersion of microcapsules was diluted 100 times in water. Diluted dispersion (1 g) was deposited into the circle on the fabric, from the edges to the center. Fabric was left to dry for 24 h.

Measurement of Perfume Release after Rubbing

AFFIRM® is a single quadrupole mass spectrometer fitted with an APCI (atmospheric chemical ionisation source and an MS-Nose interface). The operating parameters used throughout the course of these experiments are given below.

Source Temperature 105° C.
Heated transfer line 150° C.
Heated Nitrogen transfer line 105° C.
Sampling flow rate from 50 mL/min to 100 mL/min
Source gas flow rate 10 L/min
Ionisation voltage 3.8 kV
Cone voltage 14 V Prior to rubbing the sample was placed in a 1 L beaker and the headspace which was subsequently sealed with aluminum foil and allowed to equilibrate for 2 mins. The foil was then pierced with the sampling probe of the MS-Nose and the headspace sampled for 1 minute (sampling flow rate from 50 mL/min to 100 mL/min). The towel was then removed and rubbed 10 times under controlled conditions. Following the rubbing it was immediately placed in a second 1 L glass beaker and sealed again with aluminum foil and allowed to equilibrate for 2 minutes. The aluminum foil was then pierced with the MS-nose sampling probe and the headspace measured for 1 minute. The fragrance release was determined by subtracting the initial (un-rubbed) measurement from the measurement after rubbing. 3 replicates of each sample were carried out to determine the reproducibility. The results obtained from the headspace analysis before and after rubbing of the different samples are summarized in FIGS. 1 to 5.

Figure 1:
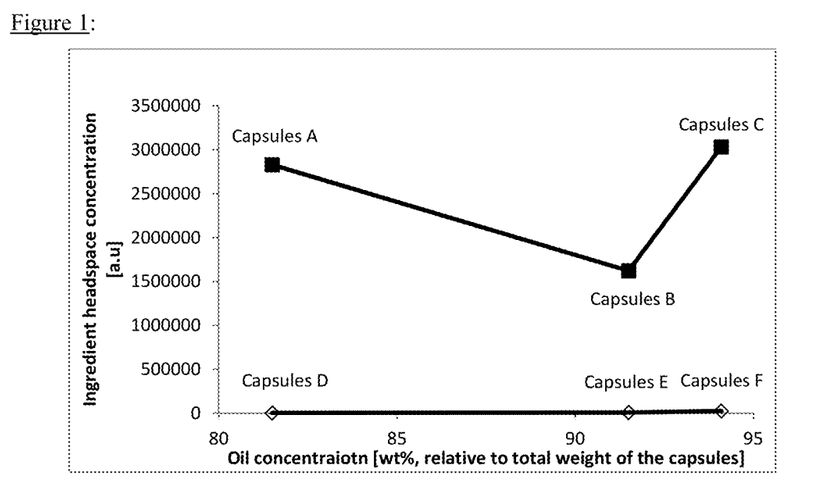
FIG. 1: Intensity of 2-methoxy-4-methylphenyl methyl carbonate released from capsules according to the invention (A, B, C), compared to the intensity of vanillin released from comparative microcapsules (D, E, F) after rubbing as a function of the oil concentration in the capsules measured by AFFIRM® (trademark from Firmenich SA)
Figure 2:
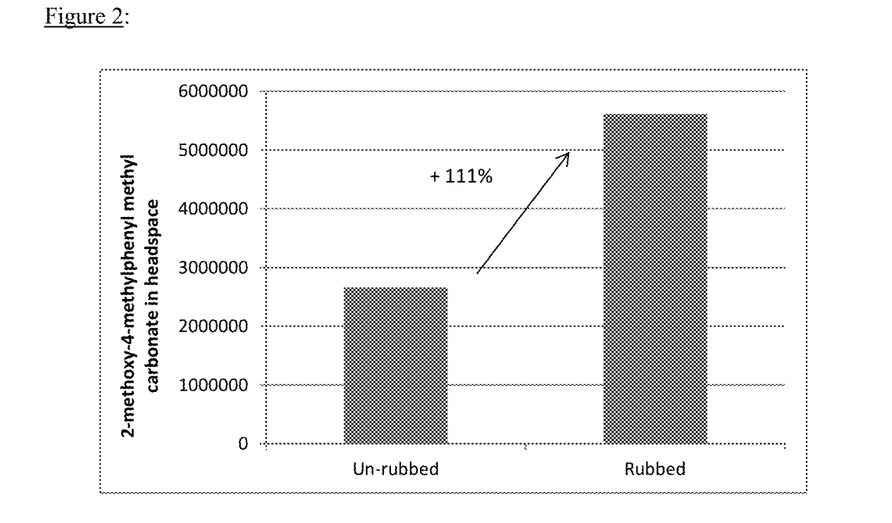
FIG. 2: Intensity of 2-methoxy-4-methylphenyl methyl carbonate released from microcapsules A according to the invention before and after rubbing.
Figure 3:
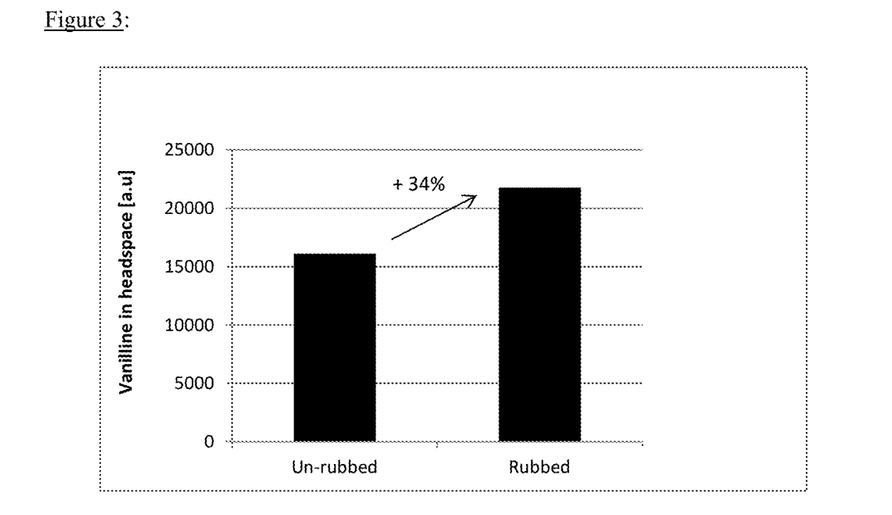
FIG. 3: Intensity of vanillin released from control microcapsules D before and after rubbing.
Figure 4:
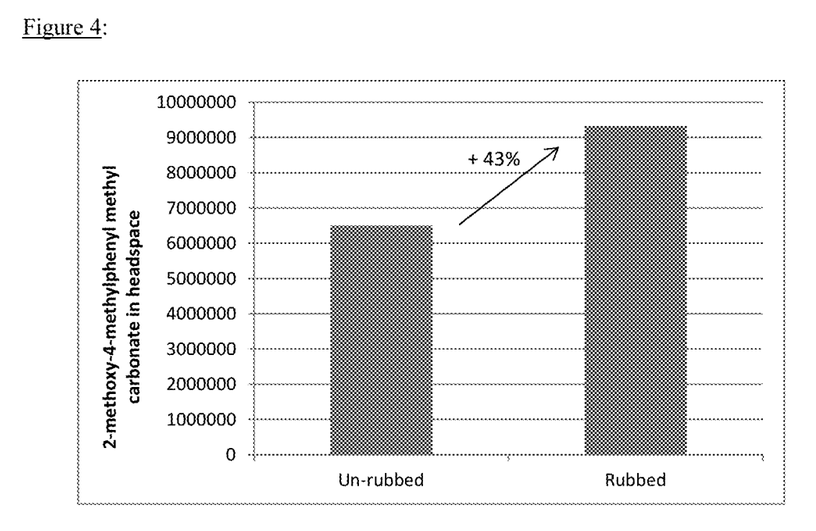
FIG. 4: Intensity of 2-methoxy-4-methylphenyl methyl carbonate released from microcapsules C according to the invention before and after rubbing.
Figure 5:
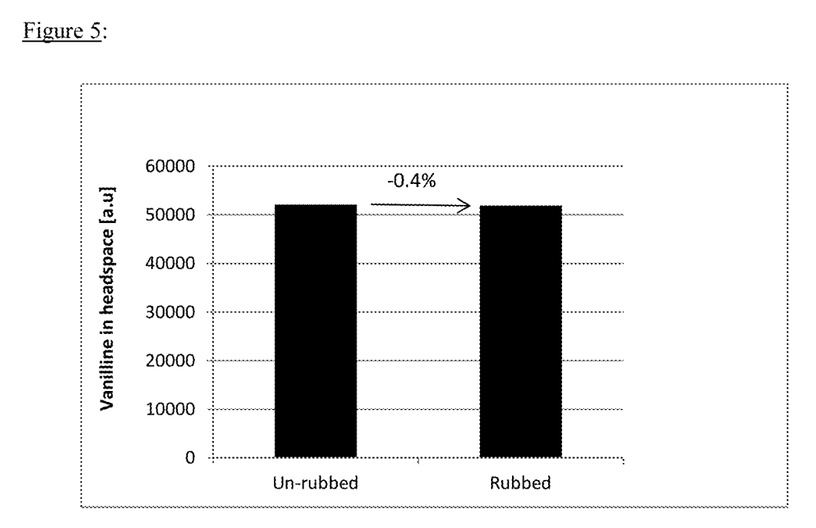
FIG. 5: Intensity of vanillin released from control microcapsules F before and after rubbing.

In FIG. 1:
- ◇ Correspond to capsules D to F containing respectively 81.5, 91.5 and 94.1% by weight of oil, and 8.2, 9.1 and 9.4% by weight of Vanillin, relative to the total weight of the microcapsule.
- ■ Correspond to Capsules A to C containing respectively 81.5, 91.5 and 94.1% by weight of oil, and 24.5, 27.4 and 28.2% by weight of 2-methoxy-4-methylphenyl methyl carbonate, relative to the total weight of the microcapsule.

Surprisingly, as shown in FIG. 1, the intensity of ingredient released after rubbing is proportionally more intense than expected for microcapsules containing 2-methoxy-4-methylphenyl methyl carbonate (capsules A to C) than for microcapsules containing vanillin (capsules D to F). Actually, the loading of capsules A to C is respectively three times higher than capsules D to F whereas the intensity after rubbing for capsules A to C is at least 100 times higher compares to capsules D to F.

FIGS. 2 to 5 show the intensity of 2-methoxy-4-methylphenyl methyl carbonate (FIGS. 2 and 4), respectively vanillin (FIGS. 3 and 5) released from microcapsules before and after rubbing. The capsules containing 2-methoxy-4-methylphenyl methyl carbonate clearly outperformed compared to vanillin capsules.

Example 3

Preparation of Melamine Microcapsules Comprising 2-Methoxy-4-Methylphenyl Methyl Carbonate of the Present Invention:

A solution of melamine-formaldehyde resins (Urecoll SMV, origin: BASF, Germany, and Cymel 9370, origin Allnex, Belgium) was prepared at room temperature (RT, pH 6.60). Acetic acid (0.18 g) was added to this solution (pH 5.10). This latter was stirred at RT for 1 h. A solution of 2-methoxy-4-methylphenyl methyl carbonate in benzyl benzoate (30 wt %, 34.62 g, origin: Firmenich SA, Switzerland) was added and the reaction mixture was stirred with Ultra-Turrax® at 24,000 rpm for 2 min. The resulting emulsion was stirred at 300 rpm with an anchor and heated at 80° C. for 1.5 h. The final dispersion was cooled down to RT and neutralized with a solution of sodium hydroxide (30 wt %, 0.45 g, pH 6.74).

Example 4

Quantification of Ingredient Imparting Vanilla Note in the Slurry—Comparative Examples with WO 2014059087 a) Preparation of Microcapsules Slurry

1) Preparation of Microcapsule Slurry of the Present Invention Comprising 2-Methoxy-4-Methylphenyl Methyl Carbonate—Microcapsule Slurry a This microcapsule slurry has been prepared as described in example 3.

ii) Preparation of Control Microcapsule Slurry Comprising Vanillin—Control Microcapsule Slurry B Control microcapsule slurry B was prepared according to protocol described in example 3. Solution of 2-methoxy-4-methylphenyl methyl carbonate was replaced by a solution of vanillin in benzyl benzoate (10 wt %, 34.62 g, origin: Firmenich SA, Switzerland).

iii) Preparation of Control Microcapsule Slurry Comprising Neobee as Described in WO2014059087—Control Microcapsule Slurry C Control microcapsule slurry C was prepared according to protocol described in example 3. Solution of 2-methoxy-4-methylphenyl methyl carbonate was replaced by neobee M5 oil (34.62 g).

b) Preparation of a Solution Comprising Vanillin as Described in WO2014059087

A solution of vanillin (2.00 g) in diisopropylene glycol (8.00 g) was prepared (Solution A). This solution A was mixed with neobee oil (0.57 g) and Tween® 20 (0.2869 g, origin: Sigma Aldrich, Switzerland) to prepare a solution B as described in document WO2014059087.

c) Preparation of Vanillin Friable Shell-Core Microcapsules Composition (Dispersion A to C) Following Process as Defined in WO2014059087 by Aging Solution B Comprising Vanillin and Microcapsule Slurry A to C Solution B as prepared above (2.50 g) was mixed with the microcapsule slurry A, B or C (47.146 g) prepared above and was aging at least 24 h to afford a white dispersion (respectively Dispersion A, Dispersion B, Dispersion C).

d) Extraction and Quantification of Dispersion A to C

These dispersions; i.e. Dispersion A and comparative Dispersion B or C (5.00 g) were extracted with ethyl acetate (5 mL) and the quantity of vanillin and/or 2-methoxy-4-methylphenyl methyl carbonate was determined by GC (Table 3). This extraction and quantification allows measuring the amount of vanillin and/or 2-methoxy-4-methylphenyl methyl carbonate which are in the slurry; i.e. not in the core of the microcapsule. The expected amount of vanillin in the slurry is 9.2 mg/ml. A lower amount of vanillin in the slurry means that a part of vanillin from solution B has diffused inside the core of the microcapsules. A higher amount of vanillin in the slurry is expected only for control dispersion B and it means that a part of vanillin from the core of the capsules has diffused outside the microcapsules. Experiments were done in triplicate.

TABLE 3

Extraction and quantification of Vanillin and/or 2-methoxy-4-methylphenyl methyl carbonate in Dispersion A of the present invention, and Comparative Dispersions B and C.

| Samples | Extracted vanillin mg/ml | Extracted 2-methoxy-4-methylphenyl methyl carbonate mg/mL | Total extracted |
|---|---|---|---|
| Dispersion A | 13.16265 | 0.468667 | 13.63131 |
| Control Dispersion B | 36.64219 | — | 36.64219 |
| Control Dispersion C | 11.85584 | — | 11.85584 |

The extraction and quantification of Dispersion A corresponding to microcapsules of the present invention aging at least 24 h into a solution of vanillin as described in WO2014059087 has shown that about 13.2 mg/ml of vanillin is in the slurry (expected amount of vanillin in the slurry is 9.2 mg/ml—the difference is in the range of expected experimental error). The amount of vanillin in the composition is not in the core of the capsule. The vanillin does not diffuse inside the core of the capsules but stays in the slurry. Furthermore, it was shown that only a small amount of 2-methoxy-4-methylphenyl methyl carbonate leaks from the core of the capsules (or is not encapsulated).

When 2-methoxy-4-methylphenyl methyl carbonate has been replaced by vanillin in the core of the capsules and that said microcapsules has been aging at least 24 h into a solution of vanillin as described in WO2014059087 (Control Dispersion B), it was shown that an important amount of vanillin largely superior to the initial amount in solution was in the slurry; i.e. not in the core of the capsule which demonstrates that a large amount of vanillin has leaked from the core of the capsules or has not been encapsulated.

The extraction and quantification of Control Dispersion C corresponding to vanillin friable shell-core microcapsules composition as described in WO2014059087 has shown that about 11.9 mg/ml of vanillin is in the slurry. This extracted amount of vanillin in the slurry means that all vanillin of the solution prepare in step b) are in the slurry after the aging. So, the majority of the amount of vanillin in the composition as defined in WO2014059087 is not in the core of the capsule contrary to the present invention wherein 2-methoxy-4-methylphenyl methyl carbonate is principally in the core of the microcapsules. It is important in order to benefit to a long lasting olfactive experience to have a majority of the perfume ingredient inside the core of the capsule and not only in the slurry.

These data showed that the stability of capsules in dispersion A is much higher than the stability of capsules from comparative dispersion B as only a small amount of 2-methoxy-4-methylphenyl methyl carbonate has been found in the slurry. As a consequence, the encapsulation of 2-methoxy-4-methylphenyl methyl carbonate affords more stable delivery system than the same capsules prepared with vanillin, which was not expected. Furthermore, these data showed that in the vanillin friable shell-core microcapsules composition as described in WO2014059087 only a tiny amount of vanillin was in the core of the microcapsule contrary to the present invention which allowed incorporating in the core of the capsule a large amount of ingredient imparting a vanillin note.

Example 4

Fabric Softener Product Comprising the Capsules of the Invention or Control Capsule and Olfactive Evaluation Thereof The liberation of vanillin or 2-methoxy-4-methylphenyl methyl carbonate was tested in a fabric softening application using a fabric softener with the following final composition:

| Stepantex ® VL90 A (origin: Stepan) | 16.5% by weight |
|---|---|
| Calcium chloride (10% aq. solution) | 0.6% by weight |
| Water | 82.9% by weight | a) Sample Containing Comparative Friable Shell-Core Microcapsule Composition of the Prior Art WO2014059087

In a vial, vanillin (0.1 g), DIPG (0.4 g), Neobee M5 (0.029 g) and tween 20 (0.014 g) were dissolved in control microcapsule slurry of example 4 a) iii) (9.42 g). The resulting dispersion (0.5 g) was dispersed in Fabric softener formulation (5.0 g). Fabric softener (0.012 g) was then dispersed in water (4.12 mL) in a vial. A wool swatch (0.88 g, Z.0537-5, Testex, Germany) was introduced into the vial and stirred for 2 minutes. Wool swatch was extracted and wrung out to obtain a weight of 2.2 g (swatch+water).

b) Sample Containing Melamine Microcapsule of the Present Invention

In a vial, microcapsules slurry of example 3 (0.1 g) was dispersed in Fabric softener formulation (10.0 g). Fabric softener (0.012 g) was then dispersed in water (4.12 mL) in a vial. A wool swatch (0.88 g) is introduced into the vial and stirred for 2 minutes. Wool swatch is extracted and wrung out to obtain a weight of 2.2 g (swatch+water).

c) Evaluation of Vanilla Intensity on Wool Swatch:

Treated wool swatches were line-dried at room temperature for 24 h. Perfume intensity was evaluated in intensity, before and after the rubbing of the swatches, by 3 panelists after 1 day, using a scale ranging from "1" (no odor) to "7" (very strong). Results are to summarized in Table 4.

TABLE 4 a) capsules evaluation on wool swatches after application of fabric softener containing capsules from the prior art WO2014059087 and from the present invention.

| Capsule | Before rubbing | After rubbing |
|---|---|---|
| WO2014059087 | 1 | 1.75 |
| Example 3 | 1 | 3 |

Results showed a stronger intensity from the capsules of the current invention and a perceivable vanilla note on the fabric after rubbing demonstrating the better performance of the capsules of the present invention compared to microcapsules composition reported in WO2014059087.

What is claimed is:

1. A microcapsule comprising
   A) a core comprising a perfume oil including a compound of formula (I)

wherein R groups represent, independently from each other, a hydrogen atom or a methyl group; and
   B) a polymeric shell surrounding said core;
   characterized in that the compound of formula (I) is present in an amount comprised between 20% and 30% by weight, relative to the total weight of the microcapsule.

2. A microcapsule according to claim 1, characterized in that the compound of formula (I) is present in an amount comprised between 25% and 29% by weight, relative to the total weight of the microcapsule.

3. A microcapsule according to claim 1, characterized in that the perfume oil consists essentially of a compound of formula (I) and a solvent.

4. A microcapsule according to claim 1, characterized in that the compound of formula (I) is 2-methoxy-4-methylphenyl methyl carbonate.

5. A microcapsule according to claim 1, characterized in that said microcapsule is formed by interfacial polymerization, by a phase separation process induced by polymerization or by coacervation.

6. A perfuming composition containing therein microcapsules as defined in claim 1, for delivering a long lasting and intense vanilla-based note.

7. A perfuming consumer product comprising the perfuming composition according to claim 6.

8. A method to confer, enhance or improve a vanilla-based odor note comprising applying microcapsules as defined in claim 1 to a surface.

9. A perfuming composition comprising
   a) as perfuming ingredient, a microcapsules as defined in claim 1;
   b) at least one ingredient selected from the group consisting of a perfumery carrier and a perfumery co-ingredient; and
   c) optionally at least one perfumery adjuvant.

10. A perfuming consumer product comprising as perfuming ingredient, microcapsules according to claim 1.

11. A perfuming consumer product according to claim 10, characterized in that the product is a perfume, a fabric care product, a body-care product, an air care product or a home care product.

12. A perfuming consumer product according to claim 10, characterized in that the consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, a shower or bath mousse, an oil or gel, a hygiene product, an air freshener, a ready-to-use powdered air freshener, a wipe, a dish detergent or a hard-surface detergent.

13. A method to confer, enhance or improve a vanilla-based odor note from a consumer product which comprises providing microcapsules as defined in claim 1 in the product and releasing the compound of formula (I) from the microcapsules in order to deliver a long lasting and intense vanilla-based note.

\* \* \* \* \*